(12) United States Patent
Reed

(10) Patent No.: US 10,700,538 B2
(45) Date of Patent: *Jun. 30, 2020

(54) PORTABLE DEVICE AND METHOD OF SUPPLYING WIRELESS POWER TO A PORTABLE DEVICE IN A STERILE ENVIRONMENT

(71) Applicant: PELETON SURGICAL, LLC, Scottsdale, AZ (US)

(72) Inventor: David John Reed, Sheffield (GB)

(73) Assignee: PELETON SURGICAL, LLC, Scottsdale, AZ (US)

( * ) Notice: Subject to any disclaimer, the term of this patent is extended or adjusted under 35 U.S.C. 154(b) by 335 days.

This patent is subject to a terminal disclaimer.

(21) Appl. No.: 15/830,347

(22) Filed: Dec. 4, 2017

(65) Prior Publication Data
US 2018/0090959 A1    Mar. 29, 2018

Related U.S. Application Data

(63) Continuation-in-part of application No. 14/987,428, filed on Jan. 4, 2016, now Pat. No. 9,837,839.

(51) Int. Cl.
  *H02J 7/00* (2006.01)
  *H02J 7/02* (2016.01)
  (Continued)

(52) U.S. Cl.
  CPC ........ *H02J 7/0044* (2013.01); *A61B 17/1628* (2013.01); *A61B 50/30* (2016.02);
  (Continued)

(58) Field of Classification Search
  CPC ........ H02J 7/0044; H02J 7/007; H02J 7/0042; H02J 7/0031; H02J 7/025; H02J 50/10;
  (Continued)

(56) References Cited

U.S. PATENT DOCUMENTS

| | | | | |
|---|---|---|---|---|
| 6,181,105 B1 * | 1/2001 | Cutolo | ................. | H02J 7/0042 320/115 |
| 2010/0114247 A1 * | 5/2010 | Snitting | ................. | A61N 1/375 607/60 |
| 2012/0112690 A1 * | 5/2012 | Stulen | ................ | A61B 18/1445 320/108 |

FOREIGN PATENT DOCUMENTS

| | | |
|---|---|---|
| JP | 2006-314181 A | 11/2006 |
| JP | 2012-520656 A | 9/2012 |

OTHER PUBLICATIONS

International Search Report of PCT/US2018/063726; dated May 29, 2019.

* cited by examiner

*Primary Examiner* — Nathaniel R Pelton
(74) *Attorney, Agent, or Firm* — Polsinelli PC

(57) ABSTRACT

A portable device and method of supplying power to the portable device may provide a sterile environment that may protect the health and safety of patients on whom the device is employed. The portable device may be charged inside of the sterile environment. The portable device may be charged using at least one chargeable battery that may be arranged internal and/or external to a portion of the portable device, or internal and/or external to the portable device. A power supply may be connected to the at least one chargeable battery and power the portable device for use. The portable device may be charged up to 100% and/or or fully charged prior to opening the sterile environment.

20 Claims, 14 Drawing Sheets

(51) Int. Cl.
  *H02J 50/10*   (2016.01)
  *A61B 50/39*   (2016.01)
  *A61B 50/30*   (2016.01)
  *A61B 50/33*   (2016.01)
  *A61B 17/16*   (2006.01)
  *A61B 17/00*   (2006.01)
  *A61B 90/00*   (2016.01)
  *A61B 50/00*   (2016.01)
  *H02J 50/12*   (2016.01)
  *H01M 10/42*   (2006.01)

(52) U.S. Cl.
  CPC .............. *A61B 50/33* (2016.02); *A61B 50/39* (2016.02); *H02J 7/0031* (2013.01); *H02J 7/025* (2013.01); *H02J 50/10* (2016.02); *A61B 17/1622* (2013.01); *A61B 2017/0046* (2013.01); *A61B 2017/00398* (2013.01); *A61B 2017/00429* (2013.01); *A61B 2017/00734* (2013.01); *A61B 2050/0065* (2016.02); *A61B 2090/0813* (2016.02); *H01M 10/4257* (2013.01); *H02J 7/00* (2013.01); *H02J 50/12* (2016.02)

(58) Field of Classification Search
  CPC .. H02J 50/00; H02J 7/0052; H02J 2007/0062; H02J 2007/0098; A61B 50/30; A61B 50/33; A61B 50/39; A61B 17/1628; A61B 17/1622; A61B 2050/0065; A61B 2090/0813; A61B 2017/00398; A61B 2017/00429; A61B 2017/00734
  USPC ................................................. 320/108, 137
  See application file for complete search history.

PORTABLE DEVICE AND METHOD OF SUPPLYING WIRELESS POWER TO A PORTABLE DEVICE IN A STERILE ENVIRONMENT

CROSS REFERENCE TO RELATED APPLICATION

This application is a continuation-in-part application of U.S. application Ser. No. 14/987,428, filed Jan. 4, 2016, the entire contents of which is incorporated herein by reference.

FIELD OF THE INVENTION

The present disclosure generally relates to a power tool and a method of supplying power to a power tool, and more particularly to a portable device powered by a chargeable battery and a method of supplying power to the portable device powered by a chargeable battery.

BACKGROUND

Medical equipment and instruments are required to maintain an aseptic condition in order to protect the safety and health of patients. With the advancement of science and technology, using electrical medical equipment has become more common. However, one problem associated with using electrical medical equipment includes difficulty with safely transporting equipment over long-distances, thereby compromising the safety and health of patients that require electrical medical equipment. Additionally, prior to being shipped, medical equipment and instruments are typically only charged between 10% and 50% of their full capacity. As such, in order to ensure medical operations are safely performed, medical equipment and instruments must be charged and require a sterile power supply. In the event of an unexpected or tragic incident, e.g., an earthquake, typhoon, blizzard, or widespread power outage, charging medical equipment may not be possible. Further, geographic locations that do not have access to an adequate power supply and/or sterile environment cannot fully charge medical equipment and instruments.

While mobile power supplies are available, existing power supply devices and methods of supplying power are not able to charge medical equipment and instruments located in a sealed and sterile environment. Rather, these power supplies and methods thereof are surrounded by dust and bacteria, and are susceptible to contact by harmful fluids. Accordingly, the sterility and safety of using these power supplies to charge electrical medical equipment and instruments is degraded and the service life is significantly reduced. Additionally, the patient's health can be compromised.

SUMMARY

Embodiments of the present disclosure may provide a method for supplying power to a portable device that may be powered by at least one chargeable battery. The method may provide sealing the portable device in a sterile environment using a first microbial barrier, and the first microbial barrier may maintain the sterile environment. The method may provide charging the portable device in the sterile environment. A power supply may be arranged to supply power to the at least one chargeable battery contained in the portable device. The method may provide sealing the portable device in the sterile environment using a second microbial barrier. The second microbial barrier may provide protection in addition to the first microbial barrier to maintain the sterile environment. The method may provide arranging the at least one chargeable battery inside of a portion of the portable device, arranging the at least one chargeable battery external to the portion of the portable device, and/or arranging the at least one chargeable battery external to the portable device. The method may provide charging the portion of the portable device to a full capacity prior to opening the sterile environment.

Embodiments of the present disclosure may provide a portable device that may be powered by at least one chargeable battery. The portable device may provide at least one microbial barrier that may be arranged to seal the portable device, and the at least one microbial barrier may maintain a sterile environment for the portable device. The portable device may provide a portion of the portable device that may include a charging port, a first tray that may be configured to receive and secure the portion of the portable device, a second tray that may be configured to receive and secure the first tray, a package that may be configured to receive the second tray, and at least one chargeable battery. The at least one chargeable battery may be configured to power the portable device. At least one cable may connect the at least one chargeable battery to the charging port, and a power supply may be arranged to supply power to the at least one chargeable battery. The at least one chargeable battery may be arranged inside of the portion of the portable device, may be arranged external to the portion of the portable device, and/or may be arranged external to the portable device. The portable device may be charged to a full capacity prior to opening the sterile environment.

A system for supplying power to a portable device may be provided in a sterile environment. The system may provide securing a portion of the portable device in a first tray, and the portion of the portable device may include a charging port for receiving power. The system may provide covering the first tray with a first microbial barrier and connecting the portion of the portable device to the first tray using a first connecting cable. The system may provide securing the first tray in a second tray and covering the second tray with a second microbial barrier. Further, the system may provide connecting the first tray and the second tray using a second connecting cable and connecting the second tray to a package using a third connecting cable. The system may provide securing the second tray in the package and supplying power to the portable device using at least one chargeable battery. The at least one chargeable battery may be arranged inside of the portion of the portable device, may be arranged external to the portion of the portable device, and/or may be arranged external to the portable device. The portable device may be charged to a full capacity prior to opening the sterile environment.

A method for supplying power to a portable device may be provided. The method may provide for sealing the portable device in a sterile environment using a first tray, a first microbial barrier, a second tray, and a second microbial barrier. The first tray may be configured to receive and secure the portable device, wherein the first microbial barrier is arranged to seal the first tray and maintain a sterile environment for the portable device. The second tray may be configured to receive and secure the first tray in the second tray, wherein the second microbial barrier is arranged to seal the second tray and maintain a sterile environment for the portable device. The method may further provide for charging the portable device in the sterile environment, wherein a power supply supplies power to at least one chargeable battery contained in the portable device. The power supply may supply power via a wireless charging station located external to the portable device. The power supply may have a transmitter operable to transmit power wirelessly to a receiver secured in the portable device. The at least one chargeable battery is operable to power the portable device.

The method may further provide inducing a magnetic field using the transmitter, wherein the transmitter is a transmitter coil operable to induce a magnetic field using an AC current. The method may further provide securing the receiver in a portion of the portable device, wherein the receiver is a receiver coil operable to receive the AC current. The method may further provide converting the AC current to a DC current via the receiver coil. The method may further provide delivering the DC current to the at least one chargeable battery via a first relay cable secured within the second tray and a second relay cable secured within the first tray, wherein the second relay cable is connected to the charging port at a first end and connected to the first relay cable at a second end opposite the first end and the first relay cable is connected to the receiver. The method may further provide maintaining the at least one chargeable battery via a charging system comprising a chip or a PCB operable to control a charge current to the at least one chargeable battery. The method may further provide disconnecting the at least one chargeable battery from the power supply via a fuse when a fuse triggering event occurs. The fuse triggering event may occur when the at least one chargeable battery receives a power greater than a power threshold. The fuse may be resettable and reusable. The method may further provide authorizing a user to reset the fuse using a trigger operable to prevent fuse resetting without an authorization.

A system for supplying power to a portable device provided in a sterile environment may be provided. The system may provide securing a portion of the portable device in a first tray, wherein the portion of the portable device includes a wireless receiver for receiving power. The system may provide covering the first tray with a first microbial barrier. The system may provide securing the first tray in a second tray. The system may provide covering the second tray with a second microbial barrier. The system may provide connecting the second tray to a package using a third connecting cable. The system may provide securing the second tray in the package. The system may provide supplying power to the portable device using at least one chargeable battery via a wireless charging station having a transmitter operable to transmit power wirelessly to the receiver. The transmitter may be a transmitter coil operable to induce a magnetic field using an AC current. The wireless receiver may be a receiver coil secured in the second tray and operable to receive the AC current. The receiver coil may be operable to convert the AC current to a DC current.

The system may further provide a first relay cable secured within the second tray and a second relay cable secured within the first tray, wherein the second relay cable is connected to the charging port at a first end and connected to the first relay cable at a second end opposite the first end the first relay cable is connected to the receiver coil. The system may further provide a charging system operable to maintain the at least one chargeable battery, the charging system comprising a chip or a PCB operable to control a charge current to the at least one chargeable battery. The system may further provide further comprising a fuse operable to disconnect the at least one chargeable battery from the power supply when a fuse triggering event occurs. The fuse triggering event may occur when the at least one chargeable battery receives power greater than a power threshold. The fuse may be resettable and reusable. The system may further provide a trigger operable to prevent fuse resetting without an authorization.

Other technical features may be readily apparent to one skilled in the art from the following figures, descriptions and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

Figure 1:
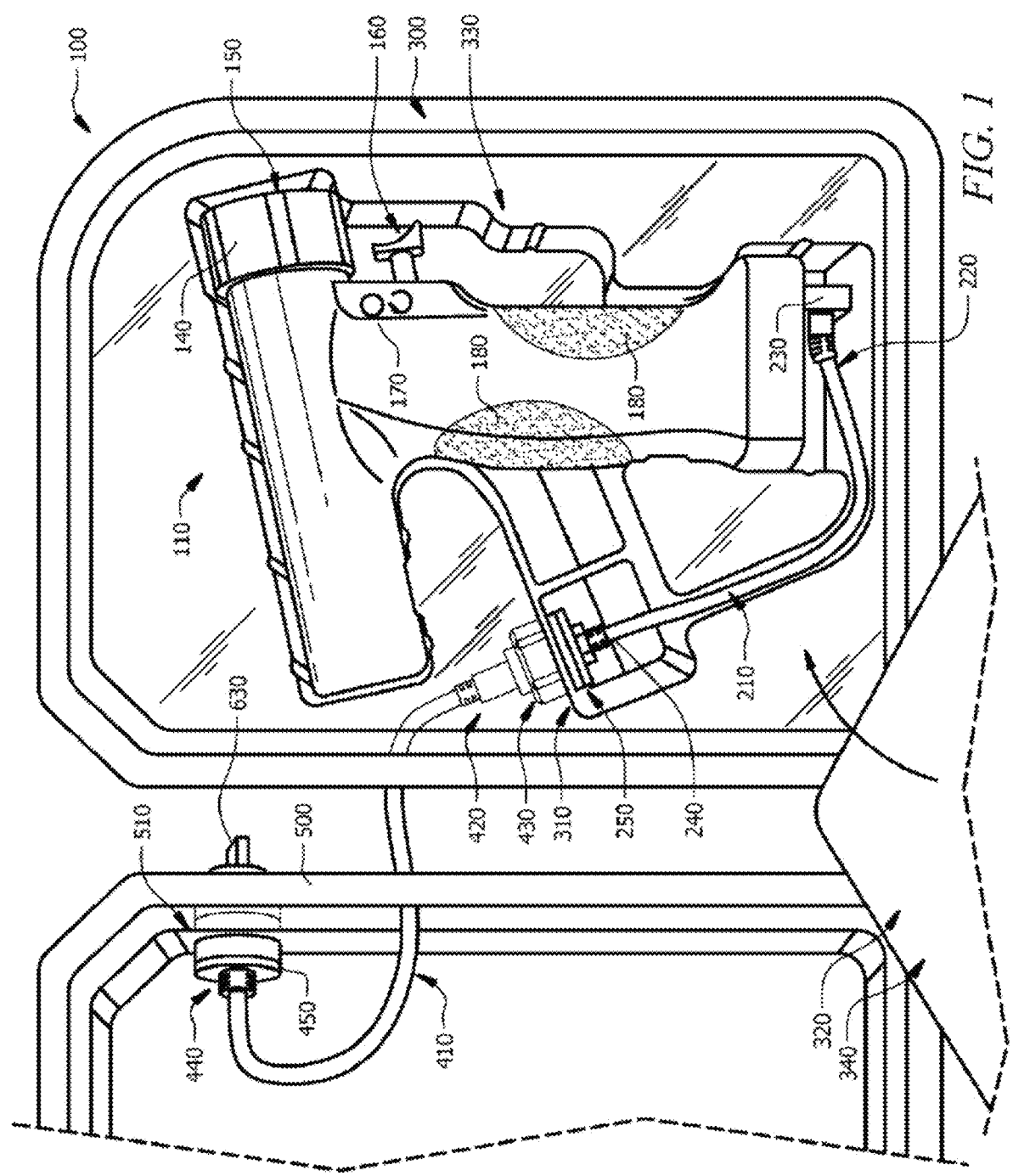
FIG. 1 depicts a portable device according to an embodiment of the present disclosure.

As shown in FIG. 1 according to an embodiment of the present disclosure, portable device that may be powered by at least one chargeable battery (hereinafter, "portable device") 100 may include portion 110 of portable device 100 that may be charged to a full capacity in a sterile environment and may be sealed by at least first microbial barrier 340. It should be appreciated that portable device 100 may be powered by a plurality of energy sources including, but not limited to, batteries and/or capacitors. Portion 110 may be secured within compartment 330 of first tray 300. Compartment 330 may be molded to the shape of portion 110 and the shape of first connecting cable 210, thereby securing portion 110 and first connecting cable 210 within first tray 300. It should be appreciated that portion 110 of portable device 100 may be a handpiece, a handle, or a gripping mechanism according to embodiments of the present disclosure. First tray 300 may be covered and sealed using first breathable lid or cover 320 and may be made from a material that may include first microbial barrier 340. First breathable lid or cover 320 may include first microbial barrier 340 to maintain a sterile environment for portable device 100. It should be appreciated that first microbial barrier 340 may provide sterile asepsis to eliminate micro-organisms from portable device 100. It should be appreciated that first tray 300 may be a blister pack that may be made of plastic or other similar material without departing from the present disclosure. It should be appreciated that first tray 300, second tray 500, and package 700 (FIG. 3 and FIG. 5) may prevent portable device 100 from sustaining damage during shipment. First connector 230 may include a male connector and may be provided at first end 220 of first connecting cable 210. It should be appreciated that a male connector may be a universal serial bus (USB), a male cord end, and/or male wire end without departing from the present disclosure. Second connector 250 of first connecting cable 210 may be provided at second end 240 opposite first end 220, and second end 240 may be secured within first wall 310 of first tray 300. Second connector 250 may include a female port that may be provided to receive third connector 430 of second connecting cable 410. It should be appreciated that a female port may include, but is not limited to, a USB port, a female cord end, and/or female wire end without departing from the present disclosure.

Figure 3:
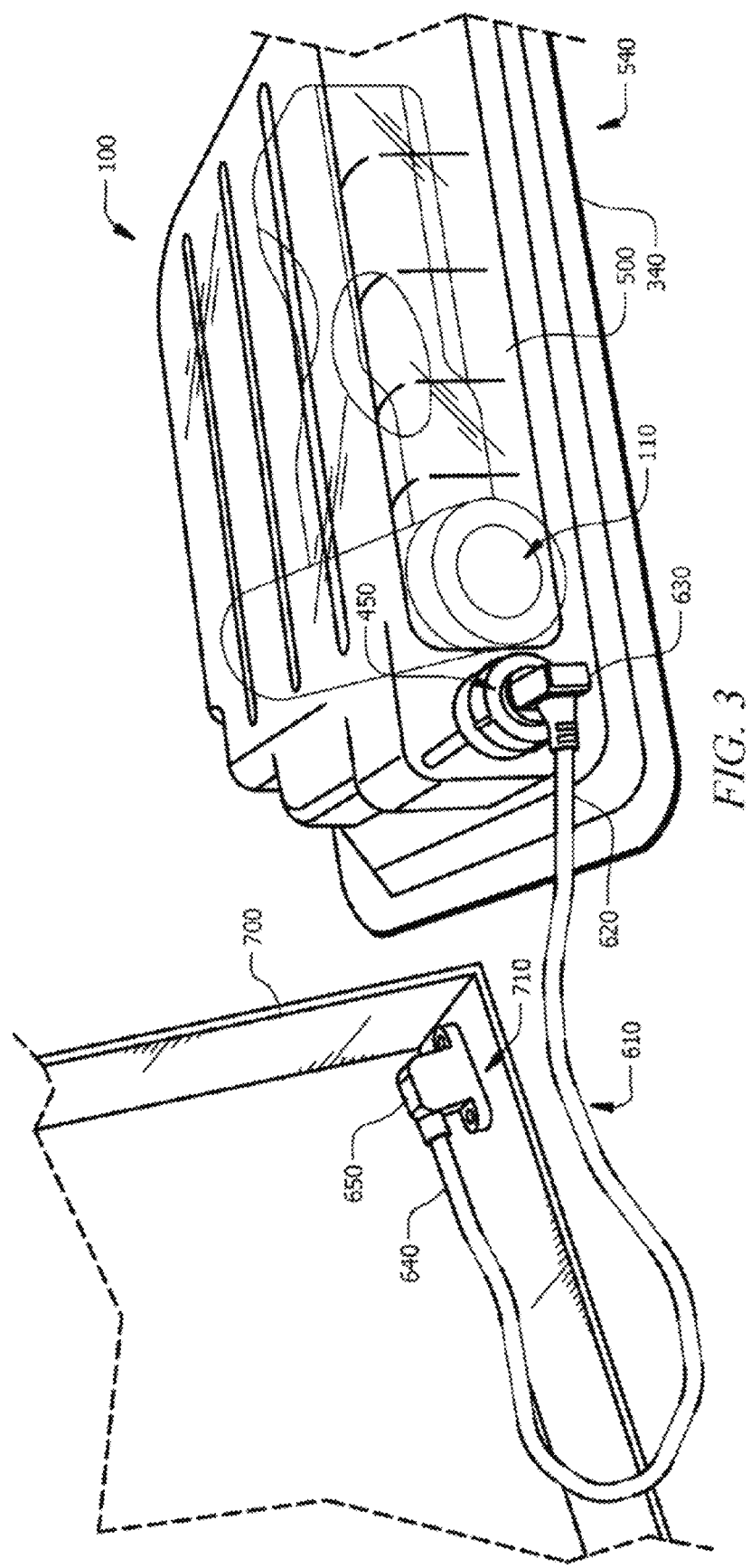
FIG. 3 depicts a perspective view of a portable device including microbial barriers and a package according to an embodiment of the present disclosure.

As shown in FIG. 1 according to an embodiment of the present disclosure, second connecting cable 410 may provide third connector 430, and third connector 430 may be provided at third end 420 of second connecting cable 410. Third connector 430 may include a male connector. Fourth connector 450 of second connecting cable 410 may include a female port that may be provided to receive fifth connector 630 of third connecting cable 610 (FIG. 3). It should be appreciated that first connecting cable 210 may be removed from within first wall 310 by disconnecting third connector 430 from second connector 250. Fourth connector 450 may be provided at fourth end 440 of second connecting cable 410 opposite third end 420. It should further be appreciated that second connecting cable 410 may be removed from within second wall 510 of second tray 500 by disconnecting fifth connector 630 from fourth connector 450. It should be appreciated that each connecting cable may be removed from a connection with a wall, package, or another connecting cable by unscrewing or disengaging each male-female connection. Second tray 500 may be covered and sealed using second breathable lid or cover 520 (FIG. 3) that may be made from a material that may include second microbial barrier 540 in some embodiments of the present disclosure. Second breathable lid or cover 520 may include second microbial barrier 540 to maintain a sterile environment for portable device 100. It should be appreciated that second microbial barrier 540 may provide sterile asepsis to eliminate micro-organisms from the portable device. It should be appreciated that cover 320 and cover 520 may provide a double layer of protective microbial barriers 340, 540 that may help to protect the sterility of portable device 100. It should be appreciated that a plurality of microbial barriers may be provided to create a sterile environment without departing from the present disclosure. It should further be appreciated that cover 320 and cover 520 may form a primary packaging for portable device 100 without departing from the present disclosure.

As shown in FIG. 1 according to an embodiment of the present disclosure, second wall 510 of second tray 500 may house a connection between fourth connector 450 and fifth connector 630. Fourth connector 450 may receive fifth connector 630. Fifth connector 630 may include a male connector. Sixth connector 650 may include a female port that may be accessible from an exterior of package 700 (FIG. 3) using sixth connector 650. It should be appreciated that a male connector may include, but is not limited to, a male USB connector, a male cord end, and/or male wire end and a female port may include, but is not limited to, a female USB port, a female cord end, and/or female wire end without departing from the present disclosure. Portable device 100 may be charged while inside of package 700, first tray 300, and second tray 500 by connecting power supply 800 (FIG. 4) to sixth connector 650 in embodiments of the present disclosure.

It should be appreciated that package 700, first tray 300 and second tray 500 may create a sterile barrier system (SBS). It should be appreciated that the SBS may prevent an ingress of microorganisms from reaching portable device 100, but may allow the passage of air and sterilizing media to contact portable device 100. Sterilizing media may include, but is not limited to, ethylene oxide (ETO), steam, gamma irradiation, and electron beam (eBeam), and may help to maintain a sterile environment for portable device 100 prior to use. It should be appreciated that the sterile environment may provide sterile asepsis to eliminate microorganisms from the portable device. It should further be appreciated that package 700, first tray 300 and second tray 500 may be made of material including, but not limited to, paper, laminated film, plastic, and foil that may provide a sterile barrier. It should be appreciated that third connecting cable (FIG. 3) and sixth connector 650 may detach from package 700.

It should be appreciated that package 700 may form a second packaging that may facilitate safe storage and handling of portable device 100. It should be appreciated that package 700 may contain any number of trays or primary packages without departing from the present disclosure.

It should further be appreciated that when first connecting cable 210 is detached from portable device 100, portion 110 of portable device 100 may be charged using power supply 800 (FIG. 4) that may be connected to charging port 120 (FIG. 2 and FIG. 6) using a plurality of connecting cables. Portion 110 may be fully charged while remaining in a sealed and sterile environment. Fully charging portion 110 may include charging at least one chargeable battery to a full capacity and/or up to 100% of its capacity. It should be appreciated that portion 110 may be charged without removing cover 320, without removing cover 520, and/or without opening package 700. It should be appreciated that a power supply may be delivered to portable device 100 using components including, but not limited to, connecting cables, a wireless charging pad, an induction charge, an electromagnetic field, radio waves, resonance stimulation, and low level microwave stimulation. It should be appreciated that at least one chargeable battery may be securely enclosed within portable device 100 in a sterile environment without compromising the aseptic nature of the contents of portable device 100 according to embodiments of the present disclosure. It should be appreciated that any number of batteries may be provided in series, in a battery pack, and/or assembled any form without departing from the disclosure. It should further be appreciated that at least one chargeable battery may be provided inside portion 110, external to portion of portable device 110, and/or external to portable device 100 without departing from the present disclosure. It should also be appreciated that batteries may include, but are not limited to, rechargeable batteries, storage batteries, a secondary cell, and/or an accumulator that can be charged, discharged, and recharged any number of times.

Figure 6:
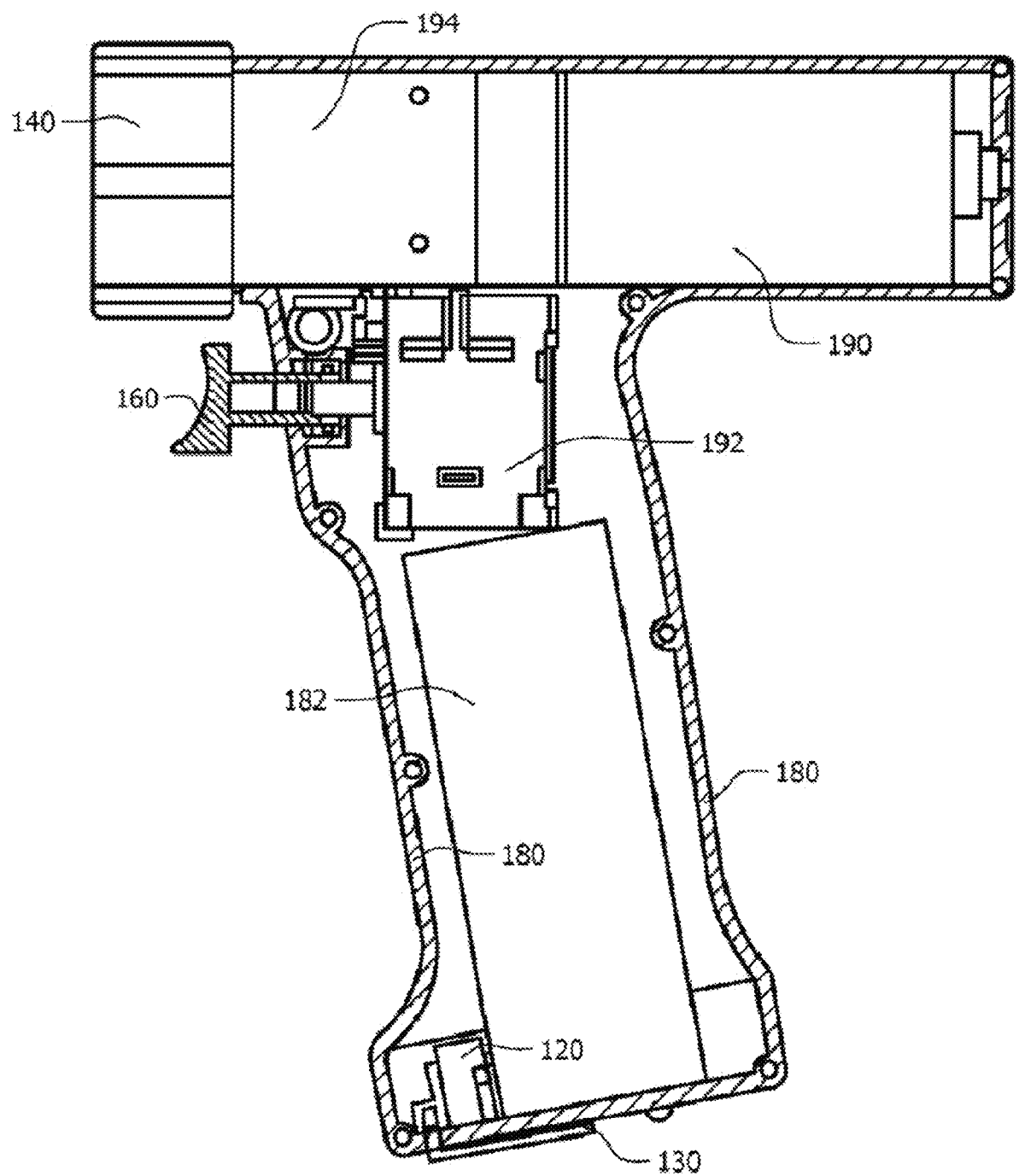
FIG. 6 depicts a sectional view of a portion of the portable device according to an embodiment of the present disclosure.

According to an embodiment of the present disclosure, as shown in FIG. 1, portion 110 of portable device 100 may provide attachment release ring 140, attachment coupling 150, and trigger 160. Attachment release ring 140 may rotate to a locked position and an unlocked position in embodiments of the present disclosure. Lock 170 may be provided to set attachment release ring 140 in the locked or in the unlocked position. It should be appreciated that lock 170 may be provided to lock the interior of attachment coupling 150 so that attachment coupling 150 may rotate in a clockwise direction or in a counterclockwise direction without departing from the present disclosure. It should be appreciated that a spring-loaded collar may be included in portable device 100 and may engage an attachment. It should further be appreciated that a spring-loaded collar may be pulled backwards along a central axis of portion 110, and when the spring-loaded collar is released, it may spring forward and securely hold the attachment in place. It should also be appreciated that an attachment may automatically engage with internal drive shaft 194 (FIG. 6). It should be appreciated that an attachment may be removed from attachment coupling 150 by pulling a spring-loaded collar backwards along a central axis of portion 110, and may provide for easily removing the attachment. Trigger 160 may be provided to vary the speed of rotation of the interior of attachment coupling. It should be appreciated that trigger 160 may be provided to control the direction of rotation of the interior of attachment coupling 150 in a clockwise direction or in a counterclockwise direction without departing from the present disclosure. It should be appreciated that portion 110 may provide a variable-speed trigger and an instant-reverse trigger in some embodiments of the present disclosure. Portion 110 may also provide at least one grip 180 that may stabilize portion 110 in the user's hands without departing from the present disclosure. It should be appreciated that the at least one grip 180 may be textured.

Figure 2:
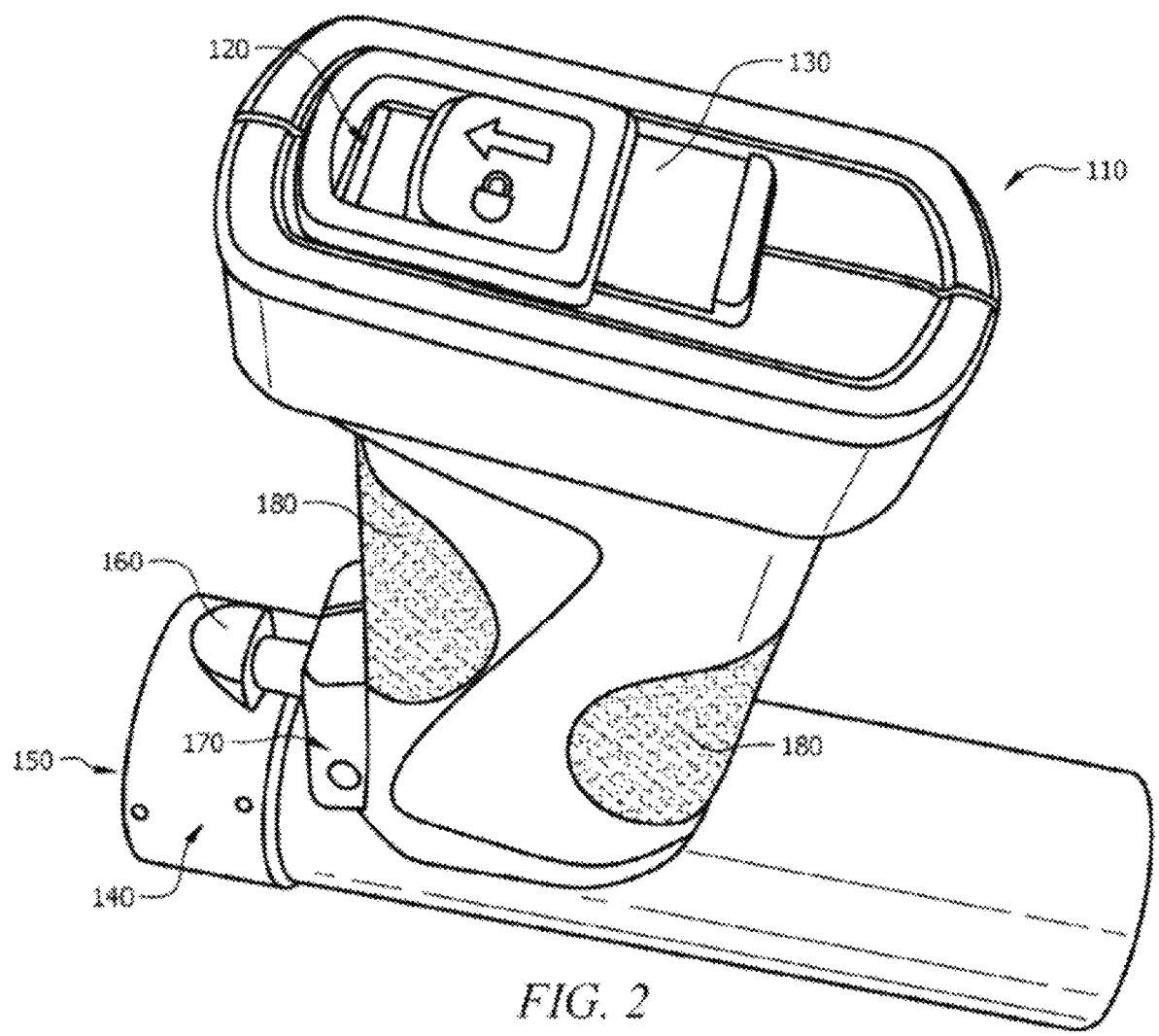
FIG. 2 depicts a perspective view of a portion of the portable device according to an embodiment of the present disclosure.

As shown in FIG. 2 according to an embodiment of the present disclosure, portion 110 may provide charging port 120 and charging port cover 130. Charging port 120 may include a female port that may be provided to receive first connector 230 (FIG. 1 and FIG. 5), and charging port 120 may be covered and protected by charging port cover 130. It should be appreciated that a female port may include, but is not limited to, a female USB port, a female cord end, and/or female wire end without departing from the present disclosure. It should be appreciated that charging port cover 130 may slide between a locked position and unlocked position 130 in embodiments of the present disclosure. It should be appreciated that the locked position may prevent first connecting cable 210 (FIG. 1 and FIG. 5) or another cable from attaching to charging port 120.

According to an embodiment of the present disclosure, as shown in FIG. 3, fourth connector 450 may receive fifth connector 630. Fifth connector 630 may include a male connector and may be provided at fifth end 620 of connecting cable 610. Sixth connector 650 may be provided at sixth end 640 of connecting cable 610 and may include a female port that may be accessible from an exterior of package 700 using sixth connector 650. Wall 710 of package 700 may house sixth connector 650. It should be appreciated that package 700 may include at least one pre-installed connecting cable without departing from the present disclosure.

Figure 4:
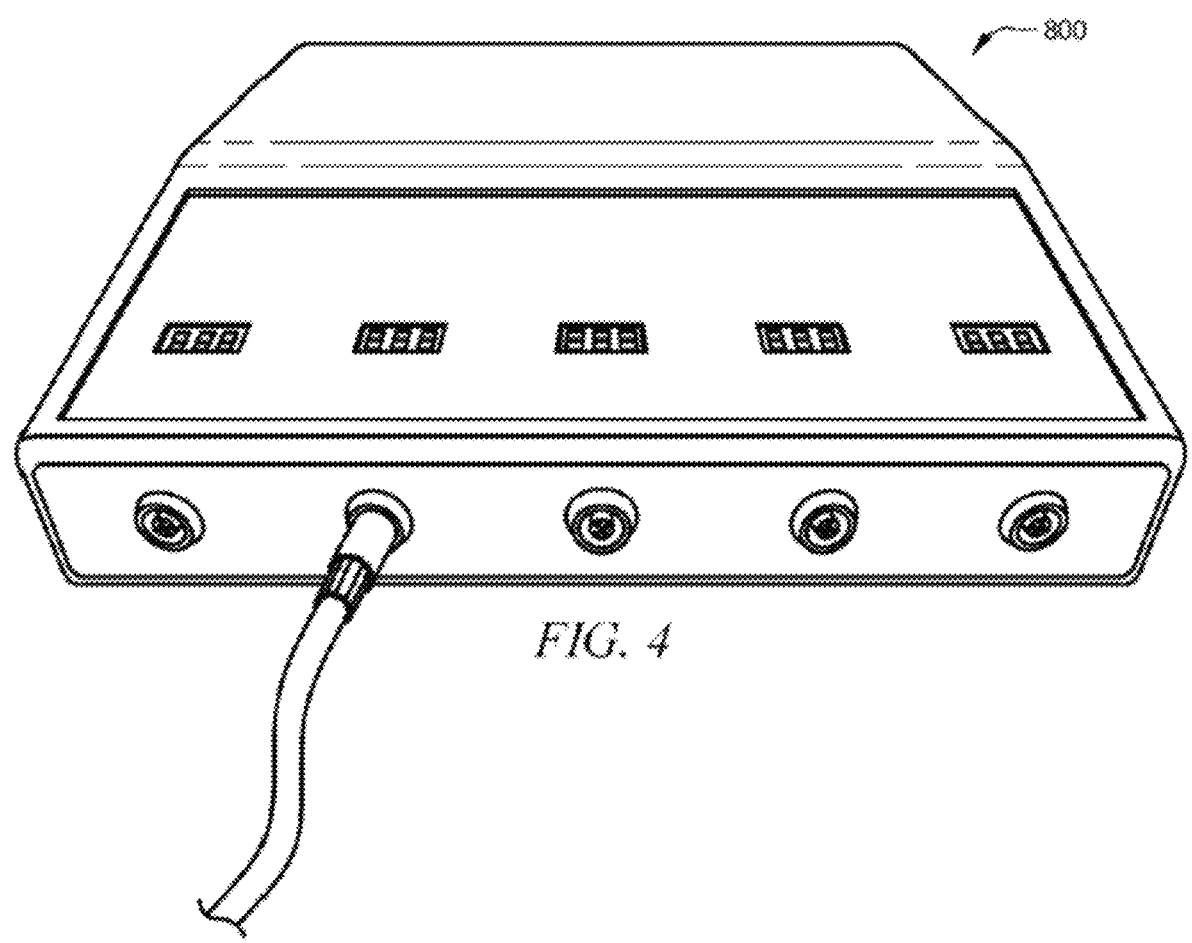
FIG. 4 depicts a power supply according to an embodiment of the present disclosure.

According to an embodiment of the present disclosure, as shown in FIG. 4, power supply 800 may be connected to the portable device and may read the charge level of the batteries. Power supply 800 may shut down when a full charge is reached, and may indicate to the user when portion 110 has attained a full charge, such as through an LED window. It should be appreciated that power supply 800 may be a battery charger in some embodiments of the present disclosure. It should be appreciated that any type of display window may be incorporated into power supply 800 without departing from the present disclosure. It should be appreciated that the charge level may indicate whether portion 110 is charged to a full capacity. It should be appreciated that a power supply may be provided within the sterile environment or external to the sterile environment according to embodiments of the present disclosure.

Figure 5:
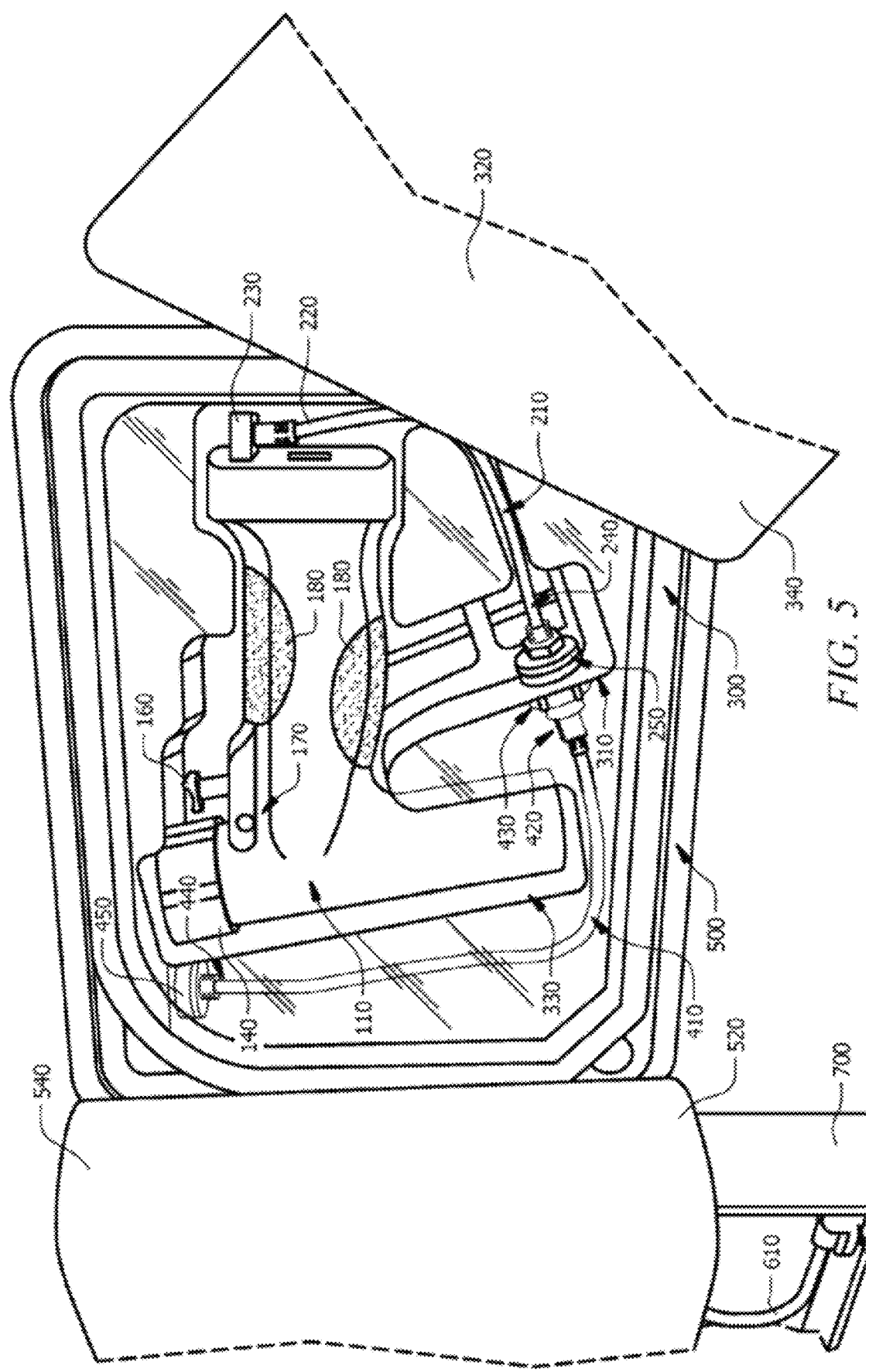
FIG. 5 depicts a portable device including open microbial barriers according to an embodiment of the present disclosure.

As shown in FIG. 5 according to an embodiment of the present disclosure, a portable device may provide cover 320 and cover 520 that may be opened and/or removed from first tray 300 and second tray 500, respectively. After removing cover 320 and cover 520, a user may remove portion 110 from compartment 330 and use portion 110 as desired. It should be appreciated that portion 110 may be removed from compartment 330 with up to 100% supply of power. It should further be appreciated that portion 110 may be charged when removed from compartment 330 without departing from the present disclosure.

As shown in FIG. 6 according to an embodiment of the present disclosure, portion 110 may provide battery 182. Battery 182 may be arranged inside of portion 110 and may be charged by connecting a cable to charging port 120. Portion 110 may include motor 190 and control panel 192. Motor 190 may control the speed of attachments that may be provided inside of attachment coupling 150. Control panel 192 may provide the electrical components required to operate at least trigger 160, motor 190, and attachment coupling 150. Internal drive shaft 194 may be connected to attachment coupling 150 and provide for an engagement of portable device 100 with an attachment. It should be appreciated that an engagement with an attachment may be accomplished using a spring-loaded collar without departing from the present disclosure.

It should be appreciated that each end of each connecting cable may be secured within a respective wall or package using mechanically compressed seals, glue, and/or a similar sealing agent that may be provided to maintain microbe-free connections. It should be appreciated that attachment coupling 150 may be provided to receive an attachment. It should be appreciated that an attachment may be selected from a plurality of attachment types and inserted into attachment coupling 150. The plurality of attachment types may include, but are not limited to, saw blades, wire/pin drivers, and drill chucks. It should further be appreciated that an attachment may be inserted into attachment coupling 150 when lock is in use. The end of the attachment provided inside of attachment coupling 150 may engage an interior of attachment coupling 150 and maintain a secured position. It should be appreciated that a free end of the attachment that is opposite of the end of attachment disposed within attachment coupling 150 may be pulled slightly to ensure that the attachment is secured inside of attachment coupling 150.

It should be appreciated that when attachment release ring 140 is rotated to unlocked position, an attachment may be removed by pulling the attachment away from attachment coupling 150. It should be appreciated that when the portable device is locked, injury to patients may be prevented. When coupling attachments, removing attachments, and/or before laying the portable device down, the portable device may be locked and may prevent injury to a user and/or patient.

It should be appreciated that portion 110 and any attachments thereto may cool down following a maximum time of constant use. The maximum time of constant use and a minimum time of non-use may be predetermined time periods. For example, the maximum time of constant use for drilling may be 60 seconds, and the minimum time of non-use may be 60 seconds over nine cycles. Regarding sawing, for example, the maximum time of constant use for drilling may be 30 seconds, and the minimum time of non-use may be 60 seconds over nine cycles. It should be appreciated that additional portable devices may be used if extended periods of constant use are required. It should be appreciated that the temperature of portable device 100 may be controlled and may prevent overheating of the device and harm to patients.

It should be appreciated that portable device 100 may be a battery-driven tool system that may be used for medical procedures including, but not limited to, drilling, reaming, pin and wire placement, and cutting bone and hard tissue. It should be appreciated that portable device 100 may be operated for non-medical use including, but not limited to, construction, household-use, and food preparation. It should be appreciated that portable device 100 may provide power for immediate use after opening cover 320, cover 520, and/or package 700. It should be appreciated that portable device 100 may provide cost advantages over reusable portable devices. It should further be appreciated that a portable device according to embodiments of the present disclosure may be used one time and may be recycled and/or discarded after use. It should be appreciated that portable device 100 may eliminate a need for maintenance and lubrication. It should also be appreciated that a portable device according to embodiments of the present disclosure may eliminate a need for back-up batteries and/or a back-up power supply. It should further be appreciated that portable device 100 may not require special processes for cleaning and/or disposal of any component.

Figure 7:
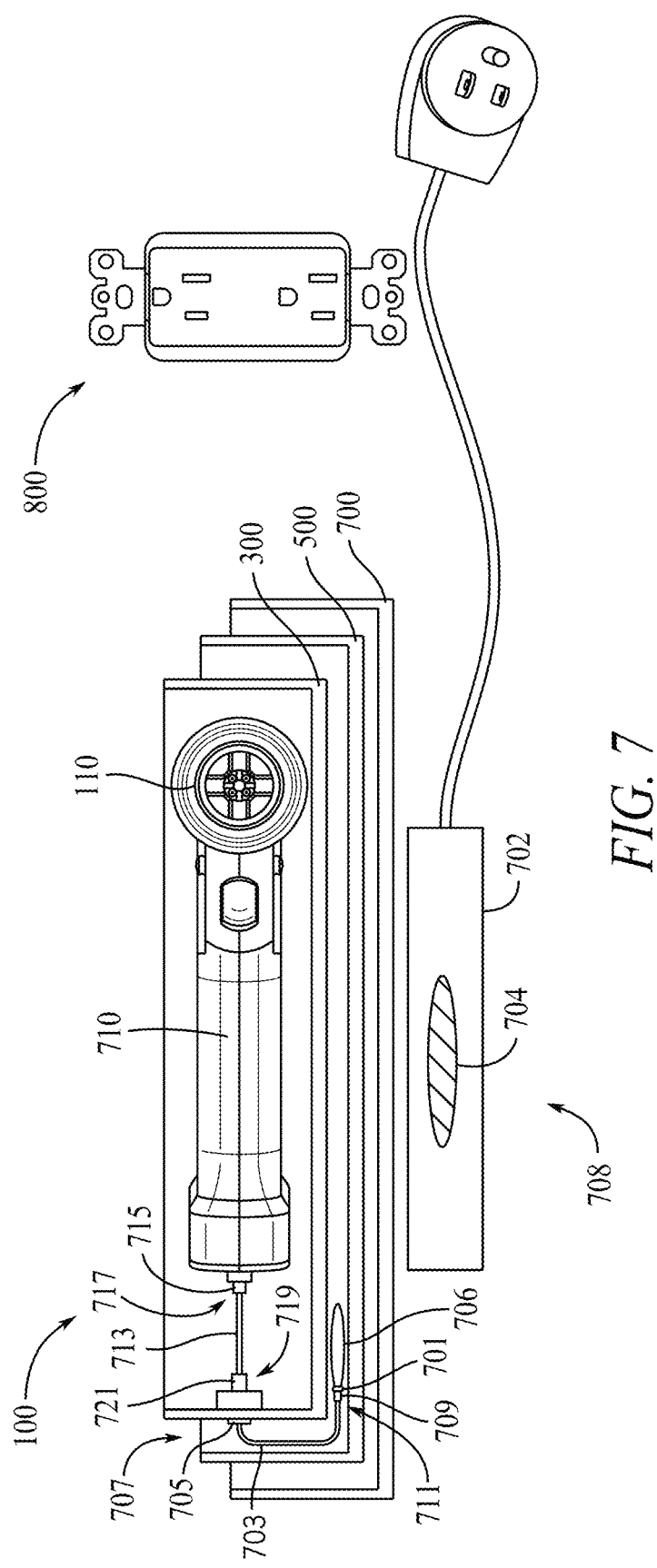
FIG. 7 depicts a top view of a portable device and a wireless charging station utilizing induction charging according to an embodiment of the present disclosure.

As shown in FIG. 7 according to an embodiment of the present disclosure, a portable device 100 may have a wireless charging station 708 using an induction charge to charge the at least one chargeable battery 710 wirelessly. The wireless charging station 708 may include a sender coil 704 secured in a charging plate 702 and operable to induce a magnetic field using an AC current. A receiver coil 706 may be secured in the second tray 500 of the portable device 100 and operable to receive and convert the AC current into a DC current. The receiver coil 706 may include a receiver connector 701 operably coupled to a relay cable 703 secured in the first tray 300. The receiver connector 701 may include a male connector provided at an end of the receiver coil 706.

The first relay cable 703 may have a first relay connector 705. The first relay connector 705 may include a male connector provided at a first end 707 of the first relay cable 703 operably coupled to a second relay cable 713. It should be appreciated that the male connector may be a universal serial bus (USB), a male cord end, and/or male wire end without departing from the present disclosure. A second relay connector 709 of the first relay cable 703 may be provided at a second end 711 opposite the first end 707. The second relay connector 709 may include a female port that may be provided to receive the receiver connector 701 of the receiver coil 706. It should be appreciated that the female port may include, but is not limited to, a USB port, a female cord end, and/or female wire end without departing from the present disclosure.

The second relay cable 713 may have a first relay connector 715. The first relay connector 715 may include a male connector provided at a first end 717 of the second relay cable 713. The male connector may be received in the female port of the charging port 120, operably coupling the second relay cable 713 to the at least one chargeable battery 710. A second relay connector 721 of the second relay cable 713 may be provided at a second end 719 opposite the first end 717, and the second end 719 may be secured within the first wall 310 of the first tray 300. The second relay connector 721 may include a female port that may be provided to receive the first relay connector 705 of the first relay cable 703. The power is delivered from the receiver coil 706 to the at least one chargeable battery 710 via the first relay cable 703 and the second relay cable 713.

It should be appreciated that the receiver coil 706 may be located within the portion 110 of the device 100 if the receiver coil 706 is within an air gap of the sender coil 704. Alternatively the receiver coil 706 may be located anywhere within or exterior to the packaging 700, but nearer to the sender coil 704, if the air gap is too wide to the device 100 to guarantee a sufficiently strong signal, in which case a relay cable or cables can be employed to complete the connection.

Figure 8:
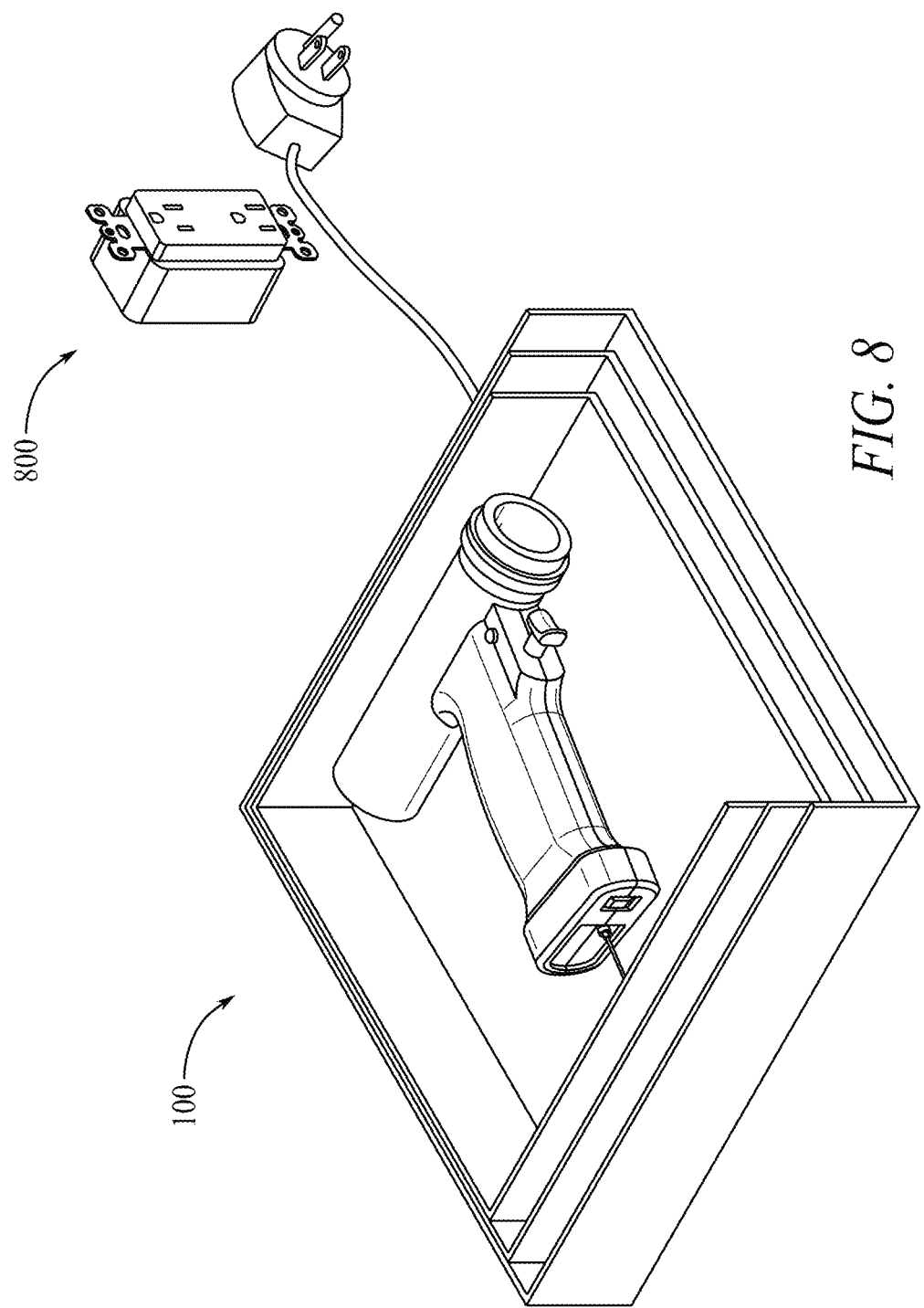
FIG. 8 depicts a top isometric view of a portable device and a wireless charging station utilizing induction charging according to an embodiment of the present disclosure.

FIG. 8 illustrates the portable device 100 charging via induction charging wherein the portable device 100 can be simply placed on top of the charging plate 702 (not visible) for charging. Once the portable device 100 is charged, the portable device can be simple picked up or removed from the charging plate 702.

Figure 9:
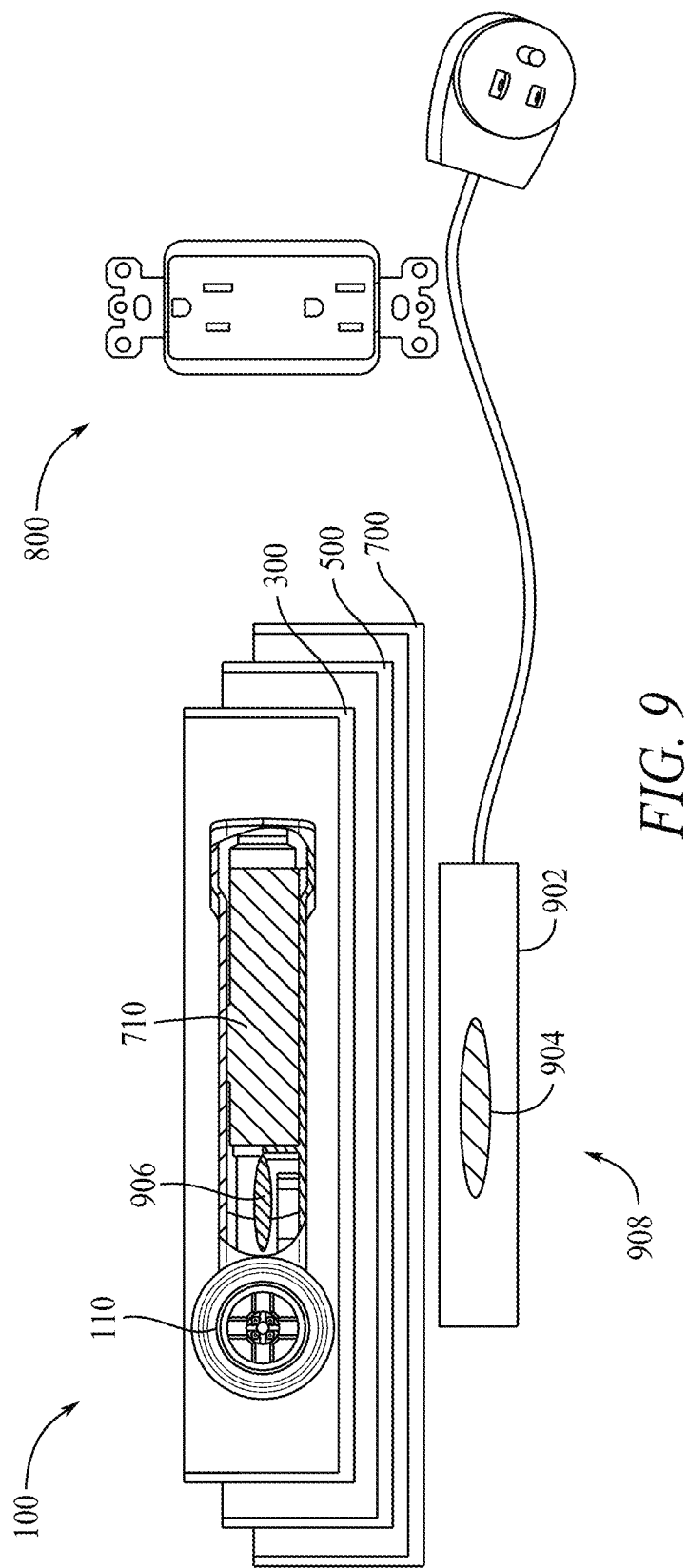
FIG. 9 depicts a top view of a portable device and a wireless charging station utilizing magnetic resonance charging according to an embodiment of the present disclosure.

As shown in FIG. 9 according to an embodiment of the present disclosure, a portable device 100 may have a wireless charging station 908 using magnetic resonance to charge the at least one chargeable battery 710 wirelessly. The wireless charging station 908 may include a sender coil 904 secured in a charging plate 902 operable to induce an oscillating magnetic field using an oscillating AC current. A receiver coil 906 may be secured in the portion 110 of the portable device 100 and operable to receive and convert the oscillating AC current into a DC current. It should be appreciated that the receiver coil 906 may be positioned anywhere within or outside the portable device 100. For example, the receiver coil 906 may be secured within the second tray 500, the first tray 300, the package 700 or may be secured outside the package 700 without deviating from the scope of the present disclosure.

Figure 10:
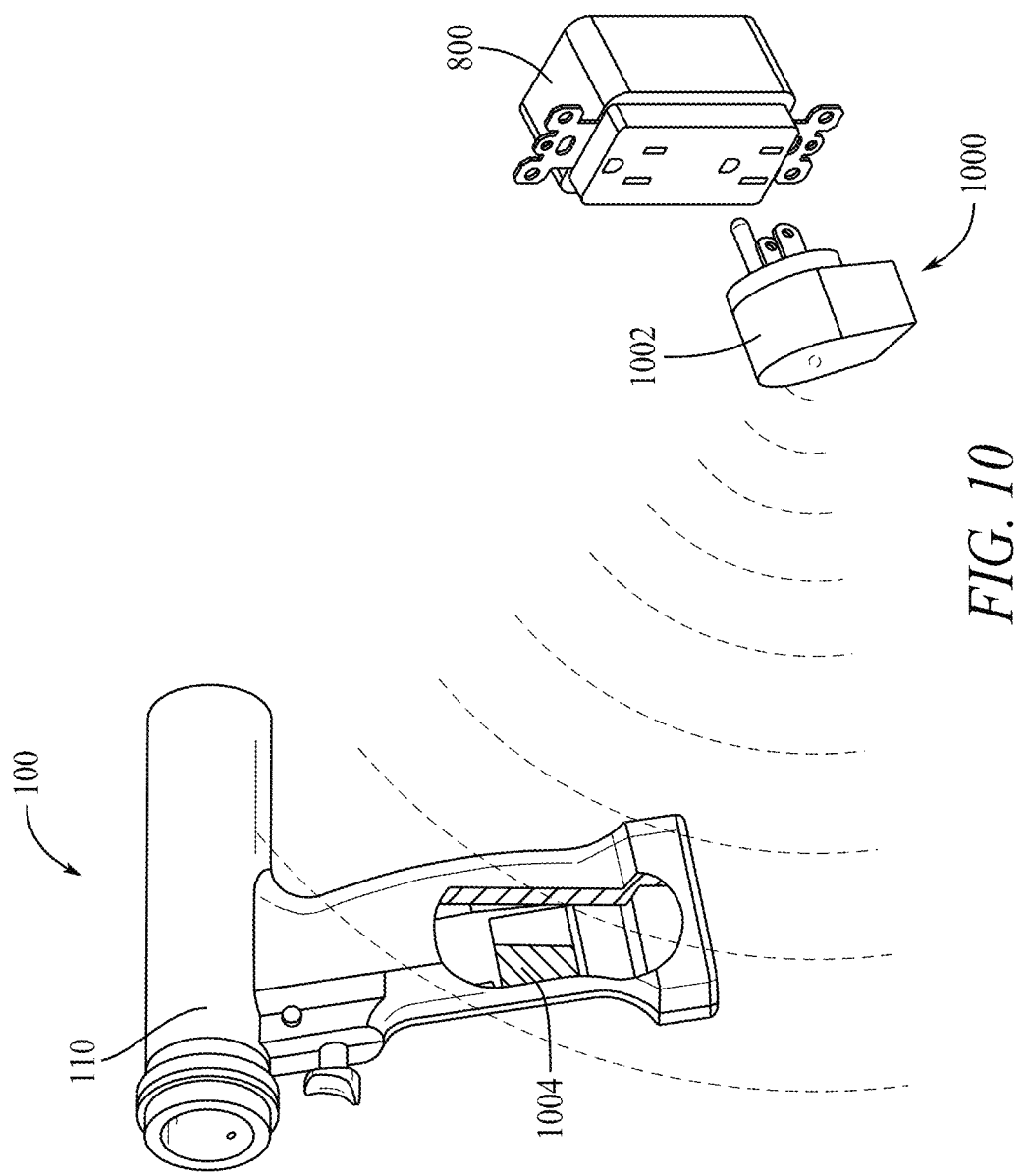
FIG. 10 depicts a top view of a portable device and a wireless charging station utilizing radio frequency charging according to an embodiment of the present disclosure.

As shown in FIG. 10 according to an embodiment of the present disclosure, a portable device 100 may have a wireless charging station 1000 using radio frequency to charge the at least one chargeable battery 710 wirelessly. The wireless charging station 1000 may include a radio frequency transmitter 1002 operable to send a low-wattage radio wave signal. A radio frequency receiver 1004 may be secured in the portion 110 of the portable device 100 and operable to receive and convert the signal into a DC current to charge the at least one chargeable battery 710. It should be appreciated that the radio frequency receiver may be positioned anywhere within or outside the portable device 100. For example, the radio frequency receiver may be positioned within the second tray 500, within the first tray 300, within the package 700, or outside the package 700 without deviating from the scope of the present disclosure.

Figure 11:
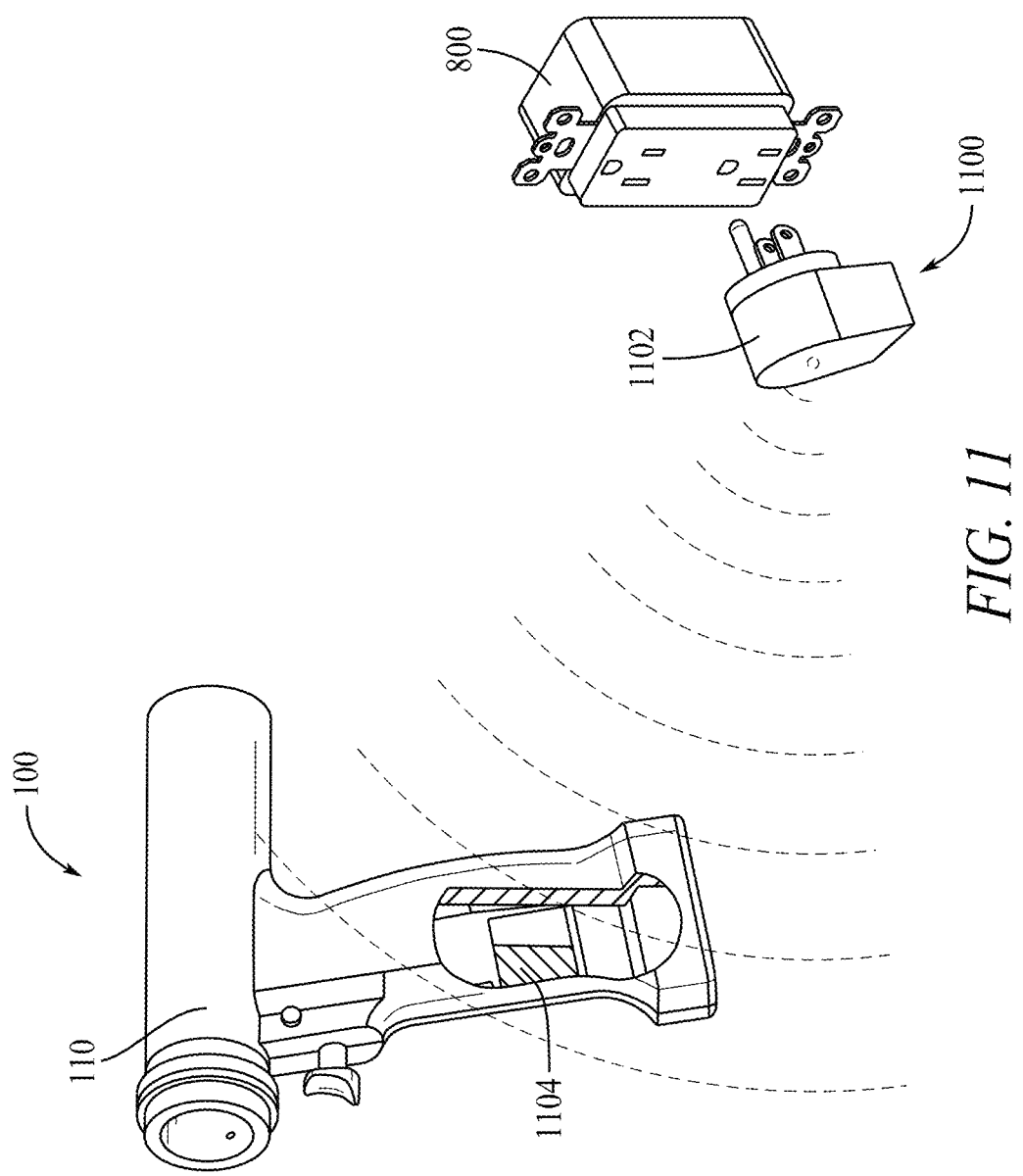
FIG. 11 depicts a top view of a portable device and a wireless charging station utilizing microwave stimulation charging according to an embodiment of the present disclosure.

As shown in FIG. 11, a portable device 100 may have a wireless charging station 1108 using microwave stimulation to charge the at least one chargeable battery 710 wirelessly. The wireless charging station 1108 may include a microwave emitter 1102 operable to send microwaves. A rectenna 1104 comprising a combined antenna and rectifier may be secured in portion 110 of the portable device 100 and operable to receive and convert the microwave into a DC current. It should be appreciated that the rectenna 1104 may be positioned anywhere within or outside the portable device 100. For example, the rectenna 1104 may be positioned within the second tray 500, the first tray 300, the package 700, or outside the package 700 without deviating from the scope of the present disclosure.

Figure 12:
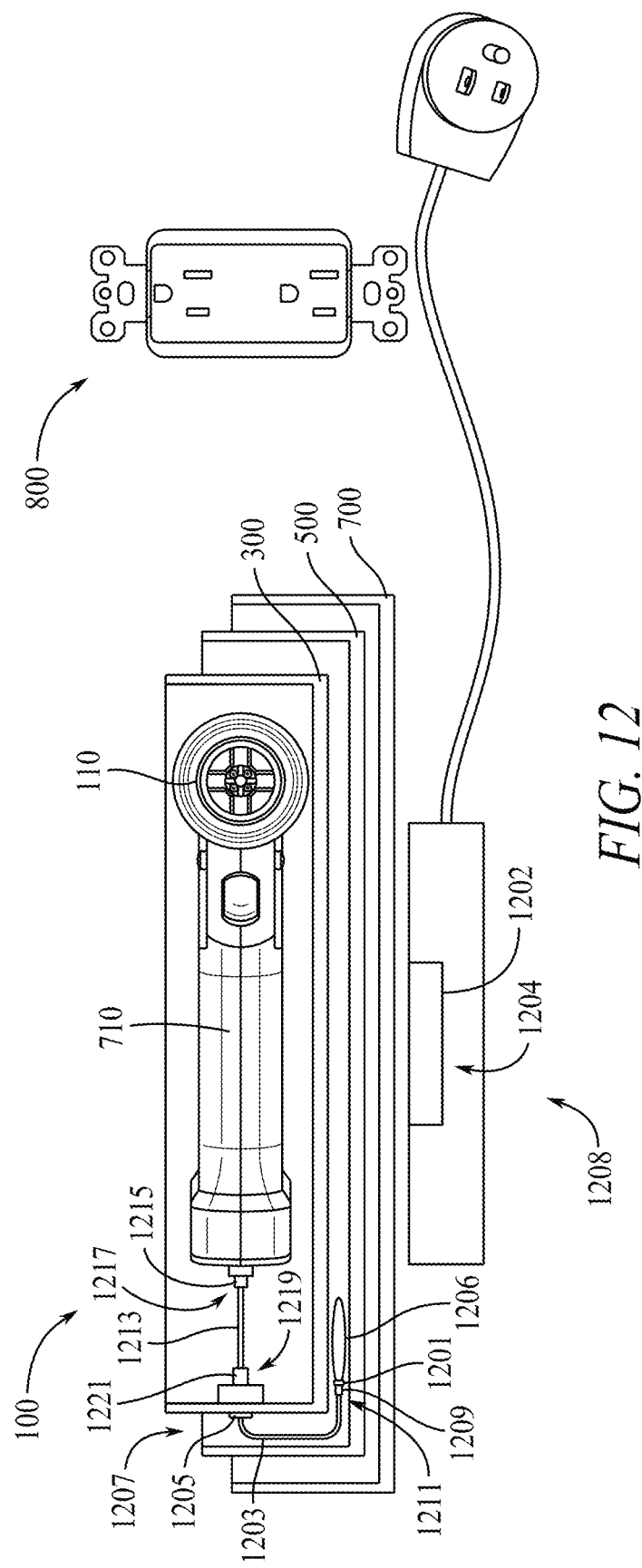
FIG. 12 depicts a top view of a portable device and a wireless charging station utilizing capacitive coupling according to an embodiment of the present disclosure.

As shown in FIG. 12, a portable device 100 may have a wireless charging station 1208 using capacitive coupling to charge the at least one chargeable battery 710 wirelessly. The wireless charging station 1208 may include a transmitter 1204 in the form of a transmitter patch 1202. A receiver may be secured on the package 700 and may be in the form of a receiver patch 1206. The transmitter 1204 is operable to transmit power to the receiver when the transmitter patch 1202 and the receiver patch 1206 are positioned proximate to each other to effectively form a capacitor with the intervening space acting at a dielectric. The receiver patch 1206 may include a receiver connector 1201 operably coupled to a first relay cable 1203 secured in the second tray 500. The receiver connector 1201 may include a male connector provided at an end of the receiver.

The first relay cable 1203 may have a first relay connector 1205. The first relay connector 1205 may include a male connector provided at a first end 1207 of the first relay cable 1203 operably coupled to a second relay cable 1213. It should be appreciated that the male connector may be a universal serial bus (USB), a male cord end, and/or male wire end without departing from the present disclosure. A second relay connector 1209 of the first relay cable 1203 may be provided at a second end 1211 opposite the first end 1207. The second relay connector 1205 may include a female port that may be provided to receive the receiver connector 1201 of the receiver patch 1206. It should be appreciated that the female port may include, but is not limited to, a USB port, a female cord end, and/or female wire end without departing from the present disclosure.

The second relay cable 1213 may have a first relay connector 1215. The first relay connector 1215 may include a male connector provided at a first end 1219 of the second relay cable 1213. The male connector may be received in the female port of the charging port 120, operably coupling the second relay cable 1213 to the at least one chargeable battery 710. A second relay connector 1221 of the second relay cable 1213 may be provided at a second end 1217 opposite the first end 1219, and the second end 1217 may be secured within the first wall 310 of the first tray 300. The second relay connector 1221 may include a female port that may be provided to receive the first relay connector 1205 of the first relay cable 1203. The power is delivered from the receiver patch 1206 to the at least one chargeable battery 710 via the first relay cable 1203 and the second relay cable 1213.

Figure 13:
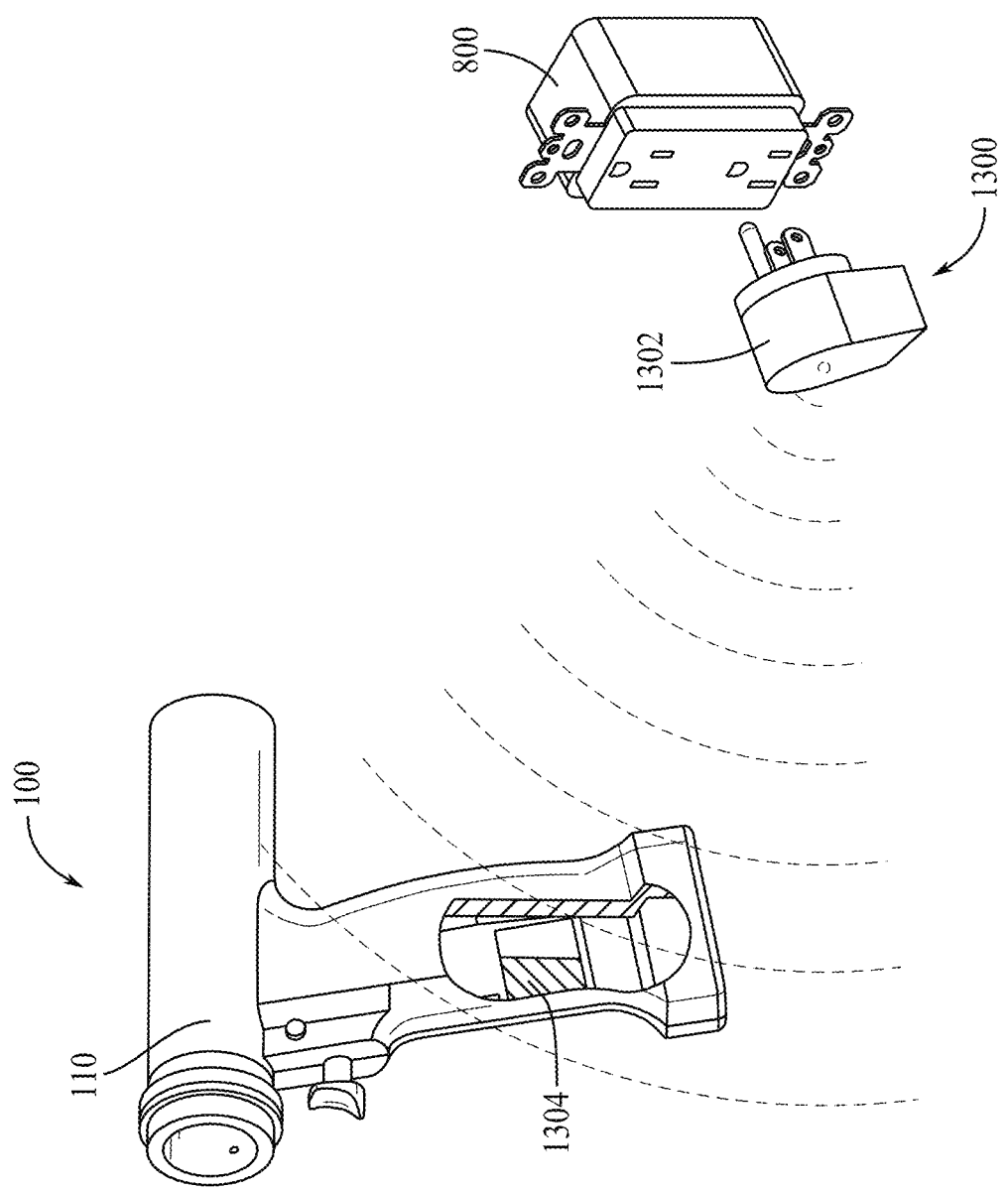
FIG. 13 depicts a top view of a portable device and a wireless charging station utilizing ultrasonic charging according to an embodiment of the present disclosure.

As shown in FIG. 13, a portable device 100 may have a wireless charging station 1300 using ultrasonic charging to charge the at least one chargeable battery 710 wirelessly. The wireless charging station 1300 may include an ultrasonic transmitter 1302 operable to transmit energy via ultrasonic waves. An ultrasonic receiver 1304 may be positioned in the portion 110 of the portable device 100 and operable to receive and convert the ultrasonic waves into a DC current. It should be appreciated that the ultrasonic receiver 1304 may be positioned anywhere within or outside the portable device 100. For example, the ultrasonic receiver 1304 may be positioned within the second tray 500, the first tray 300, the package 700, or outside the package 700 without deviating from the scope of the present disclosure.

It should be appreciated that a wireless charging station may charge more than one portable device 100 at a time. It should also be appreciated that the wireless charging station does not require the portable device 100 to be physically coupled to the wireless charging station and may provide convenience as the portable device 100 can be simply placed on top of the wireless charging station to charge the at least one chargeable battery 710. Furthermore, a lack of cables may also provide convenience as less space is needed to store the portable device 100 while it is charging.

Figure 14:
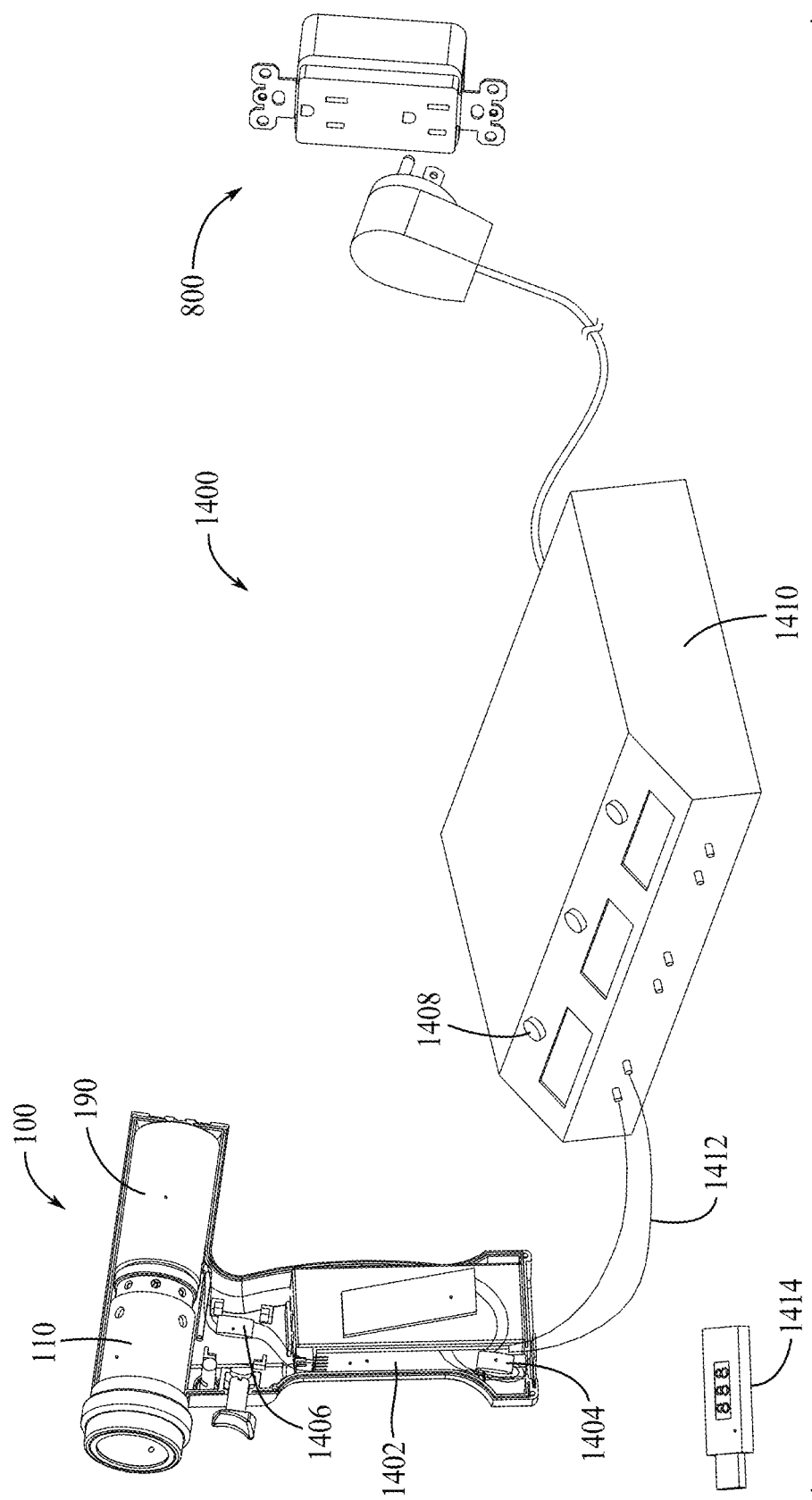
FIG. 14 depicts an intelligent charging system according to an embodiment of the present disclosure.

As shown in FIG. 14 according to an embodiment of the present disclosure, a portable device 100 may have an intelligent or smart charging system 1400 operable to monitor and maintain the at least one chargeable battery 710. The intelligent charging system 1400 may include a chip or a PCB 1402 operable to control a charge current to the at least one chargeable battery 710. The chip 1402 may be programmed to dissipate the charge current when the at least one chargeable battery 710 is full. The chip 1402 may also be programmed to provide a cut-off to the charge current to prevent damage to the at least one chargeable battery 710. The chip 1402 may also be programmed to maintain a temperature of the at least one chargeable battery 710 within a range of safe temperatures.

The intelligent charging system 1400 may further include a fuse 1404 operable to turn off or disconnect the at least one chargeable battery 710 from the power supply 800 during a fuse triggering event. The fuse triggering event may be, for example, when the at least one chargeable battery 710 receives too much power from the power supply 800, which may damage the at least one chargeable battery 710. The intelligent charging system 1400 may further include a thermal fuse 1406 operable to monitor a temperature of the motor 190 and power off the motor 190 if the temperature is greater than a threshold temperature. The fuse 1404 and the thermal fuse 1406 may be operable to be reset and reused. For example, the fuse 1404 or the thermal fuse 1406 can utilize a thermal limit wherein the fuse 1404 will disconnect the at least one chargeable battery 710 from the power supply 800 if the fuse 1404 reaches a specified temperature.

The intelligent charging system 1400 may further include a trigger 1408 operable to prevent unauthorized use or charging of the portable device 100 without authorization. The trigger 1408 may be located anywhere within or external to the device 100 or the package 700 or may be located on a monitor 1410. For example, the trigger 1408 may be used to restrict fuse resetting to authorized users. Authorization may be provided via, for example, a keypad, lock, fingerprint reader, code, or password. After authorization, the fuse 1404, thermal fuse 1406, and/or the chip or PCB 1402 may be reset.

The intelligent charging system 1400 may further use a charging cable 1412 operable to charge the device 100 and to transfer data two ways from the at least one chargeable battery 710 to the monitor 1410 and/or a controller to monitor the at least one chargeable battery 710. The charging cable 1412 may be the first, second, and third connecting cables 210, 410, 610 previously described. The monitor 1410 can be located on the package 700 and display battery information such as battery charge, estimated time to full charge, temperature, or the like. The monitor 1410 may be operable to charge the at least one chargeable battery 710 and/or reset the fuse 1404, thermal fuse 1406, and/or the chip or PCB 1402. It should be appreciated that the monitor 1410 can be located anywhere within or external the portable device 100 and can receive or send commands to the controller, chip, or PCB 1402 via a wired or wireless connection. The intelligent charging system 1400 may also include a portable monitor 1414 operable to monitor and display a status of the at least one chargeable battery 710. The portable monitor 1414 may be in the form of a USB stick or the like.

It should be appreciated that embodiments of the present disclosure may provide for usage in conflict zones or natural disasters, where charging equipment may not be possible. Further, usage may be provided in geographic locations that may not have access to an adequate power supply and/or sterile environment cannot fully charge medical equipment and instruments. However, usage in hospitals and other medical facilities may be improved insofar as devices containing tools necessary for medical procedures may be readily available off-the-shelf and for immediate use at a cost that has significant advantages over other reusable tool systems.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, and composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A method for supplying power to a portable device, the method comprising:
    sealing the portable device in a sterile environment using a first tray, a first microbial barrier, a second tray, and a second microbial barrier, wherein the first tray is configured to receive and secure the portable device, wherein the first microbial barrier is arranged to seal the first tray and maintain a sterile environment for the portable device, wherein the second tray is configured to receive and secure the first tray in the second tray, and wherein the second microbial barrier is arranged to seal the second tray and maintain a sterile environment for the portable device; and
    charging the portable device in the sterile environment, wherein a power supply supplies power to at least one chargeable battery contained in the portable device via a wireless charging station located external to the portable device having a transmitter operable to transmit power wirelessly to a receiver secured in the portable device, and wherein the at least one chargeable battery is operable to power the portable device.

2. The method for supplying power to the portable device powered by the at least one chargeable battery of claim 1, further comprising:
    inducing a magnetic field using the transmitter, wherein the transmitter is a transmitter coil operable to induce a magnetic field using an AC current.

3. The method for supplying power to the portable device powered by the at least one chargeable battery of claim 2, further comprising:
    securing the receiver in a portion of the portable device, wherein the receiver is a receiver coil operable to receive the AC current.

4. The method for supplying power to the portable device powered by the at least one chargeable battery of claim 3, further comprising:
    converting the AC current to a DC current via the receiver coil.

5. The method for supplying power to the portable device powered by the at least one chargeable battery of claim 4, further comprising:
    delivering the DC current to the at least one chargeable battery via a first relay cable secured within the second tray and a second relay cable secured within the first tray, wherein the second relay cable is connected to the charging port at a first end and connected to the first relay cable at a second end opposite the first end and the first relay cable is connected to the receiver.

6. The method for supplying power to the portable device powered by the at least one chargeable battery of claim 1, further comprising:
    maintaining the at least one chargeable battery via a charging system comprising a chip or a PCB operable to control a charge current to the at least one chargeable battery.

7. The method for supplying power to the portable device powered by the at least one chargeable battery of claim 6, further comprising:
    disconnecting the at least one chargeable battery from the power supply via a fuse when a fuse triggering event occurs.

8. The method for supplying power to the portable device powered by the at least one chargeable battery of claim 7, wherein the fuse triggering event occurs when the at least one chargeable battery receives a power greater than a power threshold.

9. The method for supplying power to the portable device powered by the at least one chargeable battery of claim 8, wherein the fuse is resettable and reusable.

10. The method for supplying power to the portable device powered by the at least one chargeable battery of claim 9, further comprising:
    authorizing a user to reset the fuse using a trigger operable to prevent fuse resetting without an authorization.

11. A system for supplying power to a portable device provided in a sterile environment, comprising:
    securing a portion of the portable device in a first tray, wherein the portion of the portable device includes a wireless receiver for receiving power;
    covering the first tray with a first microbial barrier;
    securing the first tray in a second tray;
    covering the second tray with a second microbial barrier;
    connecting the second tray to a package using a third connecting cable;
    securing the second tray in the package; and
    supplying power to the portable device using at least one chargeable battery via a wireless charging station having a transmitter operable to transmit power wirelessly to the receiver.

12. The system for supplying power to the portable device provided in the sterile environment of claim 11, wherein the transmitter is a transmitter coil operable to induce a magnetic field using an AC current.

13. The system for supplying power to the portable device provided in the sterile environment of claim 12, wherein the wireless receiver is a receiver coil secured in the second tray and operable to receive the AC current.

14. The system for supplying power to the portable device provided in the sterile environment of claim 13, wherein the receiver coil is operable to convert the AC current to a DC current.

15. The system for supplying power to the portable device provided in the sterile environment of claim 14, further comprising a first relay cable secured within the second tray and a second relay cable secured within the first tray, wherein the second relay cable is connected to the charging port at a first end and connected to the first relay cable at a second end opposite the first end and the first relay cable is connected to the receiver coil.

16. The system for supplying power to the portable device provided in the sterile environment of claim 11, further comprising a charging system operable to maintain the at least one chargeable battery, the charging system comprising a chip or a PCB operable to control a charge current to the at least one chargeable battery.

17. The system for supplying power to the portable device provided in the sterile environment of claim 16, further comprising a fuse operable to disconnect the at least one chargeable battery from the power supply when a fuse triggering event occurs.

18. The system for supplying power to the portable device provided in the sterile environment of claim 17, wherein the fuse triggering event occurs when the at least one chargeable battery receives power greater than a power threshold.

19. The system for supplying power to the portable device provided in the sterile environment of claim 18, wherein the fuse is resettable and reusable.

20. The system for supplying power to the portable device provided in the sterile environment of claim 18, further comprising a trigger operable to prevent fuse resetting without an authorization.

* * * * *